United States Patent [19]
Cohen

[11] Patent Number: 6,014,626
[45] Date of Patent: Jan. 11, 2000

[54] PATIENT MONITORING SYSTEM INCLUDING SPEECH RECOGNITION CAPABILITY

[76] Inventor: Kopel H. Cohen, 2362 Harbour Oaks Dr., Longboat Key, Fla. 34228

[21] Appl. No.: 08/695,466

[22] Filed: Aug. 12, 1996

Related U.S. Application Data

[63] Continuation-in-part of application No. 08/305,108, Sep. 13, 1994, Pat. No. 5,633,910.

[51] Int. Cl.$^7$ ...................................................... G10L 3/00
[52] U.S. Cl. ........................... 704/275; 704/271; 706/924
[58] Field of Search .................................. 395/2.79, 2.81; 379/38, 93, 106; 704/270, 275, 273, 272; 706/924, 60, 61

[56] References Cited

U.S. PATENT DOCUMENTS

| | | | |
|---|---|---|---|
| 3,727,190 | 4/1973 | Vogelman et al. | 705/3 |
| 3,774,164 | 11/1973 | Osterberg et al. | 395/850 |
| 3,882,277 | 5/1975 | De Pedro et al. | 379/106.2 |
| 3,972,320 | 8/1976 | Kalman | 600/519 |
| 4,068,097 | 1/1978 | Verriest | 379/38 |
| 4,296,756 | 10/1981 | Dunning et al. | 600/529 |
| 4,337,377 | 6/1982 | Van Riper et al. | 379/106.02 |
| 4,346,697 | 8/1982 | Cohen | 604/49 |
| 4,458,693 | 7/1984 | Badzinski et al. | 600/528 |
| 4,712,562 | 12/1987 | Ohayton et al. | 600/485 |
| 4,751,726 | 6/1988 | Hepp et al. | 379/106.02 |
| 4,803,625 | 2/1989 | Fu et al. | 600/483 |
| 4,843,377 | 6/1989 | Fuller et al. | 340/523 |
| 4,858,121 | 8/1989 | Barber et al. | 705/2 |
| 4,883,064 | 11/1989 | Olson et al. | 600/509 |
| 5,036,852 | 8/1991 | Leishman | 600/301 |

(List continued on next page.)

OTHER PUBLICATIONS

Paper entitled "Telecommunications in Managed Self Care", by Farrokh Alemi, Ph.D., presented at 17th Annual Symposium on Computer Applications in Medical Care, Oct. 31, 1993.

L. Baer, et al., "Automated Telephone Screen Survey For Depression," *JAMA*, vol. 273, No. 24, pp. 1943–1944, Jun. 28, 1995.

"VPro™ Speech Recognition on Antares™," *Dialogic® On–Line Information Retrieval System*, pp. 1–2.

"VRSoft™, Discrete,Multi–Language Speech Recognition Software", *Dialogic® On–Line Information Retrieval System*, pp. 1–3.

"Antares™ Platform Overview," *Dialogic® On–Line Information Retrieval System*, 1–3.

"2000/33, 2000/50, 6000/50 ISA Platform," *Dialogic® On–Line Information Retrieval System*, pp. 1–6.

"D/160SC–LS™ 16–Port Voice Processing & Analog Interface Board," *Dialogic® On–Line Information Retrieval System*, pp.1–9.

"VR/160™ 16–Port ASR Board," *Dialogic® On–Line Information Retrieval System*, pp. 1–7.

*Primary Examiner*—Richemond Dorvil
*Attorney, Agent, or Firm*—Kenyon & Kenyon

[57] ABSTRACT

A patient monitoring system. A patient has access to a telephone. The telephone is operated by a patient. A central monitoring system is coupled to the telephone. The central monitoring system generates questions concerning a health condition of the patient for the patient to answer using the keys of the telephone or by speaking the correct response. The central monitoring system stores answers to the questions for later retrieval. The central monitoring system can include a DTMF modem decoder for receiving and decoding DTMF tones generated by the patient using the touch-tone telephone and transmitted to the central monitoring system. The DTMF tones represent the health condition of the patient. A computer processor is coupled to the DTMF modem decoder. A voice generator is also coupled to the computer processor and generates voice output under the control of the computer processor. The voice output is transmitted to the touch-tone telephone. A database is coupled to the computer processor, storing a patient record reflecting the health condition of the patient and also storing the questions concerning the health condition of the patient.

21 Claims, 9 Drawing Sheets

U.S. PATENT DOCUMENTS

| | | | |
|---|---|---|---|
| 5,038,800 | 8/1991 | Oba | 600/509 |
| 5,065,315 | 11/1991 | Garcia | 705/2 |
| 5,099,424 | 3/1992 | Schneiderman | 205/3 |
| 5,107,831 | 4/1992 | Halpern et al. | 128/204.26 |
| 5,142,484 | 8/1992 | Kaufman et al. | 222/638 |
| 5,159,317 | 10/1992 | Brav | 340/574 |
| 5,172,698 | 12/1992 | Stanko | 600/510 |
| 5,179,587 | 1/1993 | Bock et al. | 329/93.02 |
| 5,204,670 | 4/1993 | Stinton | 340/825.54 |
| 5,207,580 | 5/1993 | Strecher | 434/238 |
| 5,253,285 | 10/1993 | Alheim | 379/52 |
| 5,289,521 | 2/1994 | Coleman et al. | 379/52 |
| 5,289,531 | 2/1994 | Levine | 379/93.23 |
| 5,305,238 | 4/1994 | Starr, III et al. | 702/176 |
| 5,321,618 | 6/1994 | Gessman | 607/5 |
| 5,357,427 | 10/1994 | Langen et al. | 364/413 |
| 5,377,258 | 12/1994 | Bro | 379/106 |
| 5,441,047 | 8/1995 | David et al. | 128/670 |
| 5,544,649 | 8/1996 | David et al. | 128/630 |
| 5,633,910 | 5/1997 | Cohen | 379/38 |
| 5,660,176 | 8/1997 | Iliff | 128/630 |
| 5,668,928 | 9/1997 | Groner | 704/243 |

PATENT MONITORING SYSTEM INCLUDING SPEECH RECOGNITION CAPABILITY

RELATED APPLICATIONS

This application is a continuation-in-part of application Ser. No. 08/305,108 filed on Sep. 13, 1994, now issued as U.S. Pat. No. 5,633,910.

FIELD OF INVENTION

The present invention is directed to a computer-implemented method and system for monitoring the health status of patients, and in particular, a method and system utilizing a standard telephone to monitor the health status of outpatients.

COPYRIGHT NOTICE

A portion of the disclosure of this patent document contains material which is subject to copyright protection. The copyright owner has no objection to the facsimile reproduction by anyone of the patent document or patent disclosure as it appears in the Patent and Trademark Office patent file or records, but otherwise reserves all copyright rights whatsoever.

BACKGROUND OF THE INVENTION

Much of the cost of providing health care is associated with time spent by medical personnel consulting with patients. Whereas equipment is relatively easy to procure, it is costly to provide the extensive training and experience required by health care professionals to enable them to provide quality health care. The growing demand for medical services at a reasonable cost has placed unprecedented demands on the health-care provider.

An outpatient usually resides at a location away from a health care provider. For example, an outpatient typically resides at home and not in the hospital where his or her doctor may have an office. Thus, the health care provider has far less opportunity to monitor the health status of an outpatient on day to day basis. Moreover, an outpatient may be required to see a doctor on a regular basis, often for simple and routine tests. In such a case, the outpatient must travel to the doctor's office or to a hospital, wait to be seen by the relevant health care provider, have the tests performed, and travel home. This inconvenient way of monitoring the health of an outpatient often does not assist the outpatient in the recovery process.

In short, patients in a hospital are regularly monitored. However, outpatients often do not receive this same level of health care.

A system is needed that will help close the gap between the level of care received by hospitalized patients and non-hospitalized patients who must visit the doctor or other health care provider for treatment. It would be advantageous if a health care provider could regularly monitor the health status of patients, including outpatients, without requiring these patients to physically travel to and make an appointment with the health care provider unless it is absolutely necessary to do so.

Many of the advantages of a remote outpatient monitoring system would be negated if the system were exceedingly costly or complex to use. Existing outpatient monitoring systems require the patient to use expensive equipment that is complex and unfamiliar to the patient. For example, many existing monitoring systems involve connecting sensors to the patient to monitor vital signs, such as blood pressure or temperature. Other systems require that one or more sensors be physically implanted into the patient's body.

Moreover, these systems often have a dedicated use, for example, they can only be used to monitor one or two physical conditions of the patient. These systems are less flexible, each being directed towards reporting a fairly narrow range of data to the health care provider, often on an intermittent basis. For example, one system may be capable of transmitting only heart rate and blood pressure; another may monitor and transmit sounds from implanted heart valves; yet another may be needed to monitor and transmit "biologic signals."

For example, U.S. Pat. No. 4,712,562 to Ohayon et al. describes a system to monitor the blood pressure and heart rate of an outpatient that requires the outpatient be provided with a special device that can take blood pressure and heart rate readings, store these readings, and later generate signals for transmission. These signals represent the stored readings and the identity of the patient. In such a system, the outpatient must be supplied with a measurement, storage and signal generating device that is programmed for use by that particular outpatient only.

U.S. Pat. No. 5,172,698 to Stanko describes a dedicated telephonic pacemaker monitoring device that has four electrode touch pads that can detect pacemaker signals or a patient's pulse and transmit the detected information over a telephone line.

U.S. Pat. No. 3,882,277 to DePedro et al. describes a portable battery-powered EKG signal detector and transmitter. EKG signals can be transmitted over a telephone link to monitoring equipment at another location.

U.S. Pat. No. 4,068,097 to Verriest describes a system that requires a specially adapted telephone set that is capable of direct communication with a central monitoring station without the handset being lifted.

U.S. Pat. No. 4,337,377 to Van Riper et al. describes an apparatus to monitor biologic signals of a patient from a telephone handset. This system requires the patient to carry a special unit that must be coupled to the telephone handset.

In the above systems, the patient has to obtain and use an electronic device capable of taking readings and transmitting data over a telephone line, often using complex communication protocols. Many of these devices have a dedicated use, i.e., are programmed for use by one patient only or are programmed for use for one set of measurements only.

Thus, there is a need for a system for remotely monitoring the health status of patients that does not require special training or complex equipment that is likely to be expensive. In particular, there is a need for a monitoring system that does not require that the patient be provided with any electronic equipment, thus allowing the patient to use communications equipment that the patient already has in his or her own home.

Some known systems used to obtain information from patients contact patients at predetermined times. There exists a need for a patient monitoring system that allows the patient to contact the central system at times and from locations convenient to the patient.

Further, there is a need for a single system that is capable of being adapted to an individual's evolving physical condition. Each patient may have different conditions that require monitoring. For example, for one patient, pulse information may be important, for another, blood pressure, and for a third patient, temperature. The health care provider needs a single system to easily monitor all conditions of all patients.

Further, as a patient's condition improves, some information may not be needed. Existing systems are not flexible and cannot easily be adapted for each patient's differing and evolving conditions.

Existing monitoring systems concentrate on obtaining information relating to physical conditions, such as blood pressure, pulse, EKG and the like. Often, for example, when a patient is taking medicine or has a psychological problem, the health care provider must additionally monitor other factors, such as how well a patient sleeps, whether the patient feels drowsy or depressed, and whether the patient has an appetite. Existing monitoring systems do not enable health care providers to remotely monitor psychological and other related conditions of a patient.

SUMMARY OF THE INVENTION

The present invention is directed to a method and system for remotely monitoring the health status of patients, in particular outpatients, using telecommunications hardware systems already likely to exist in a patient's home, such as, for example, a telephone or personal computer with a modem.

The representative embodiment of the present invention can be regarded as having two subsystems, namely, a central monitoring subsystem and a patient subsystem.

The central monitoring subsystem receives, stores and processes health information provided by one or more patients, and generates periodic reports for the relevant health care providers. Typically, the central monitoring subsystem is located in a central location so as to be accessible by telephone to all patients who require monitoring. Further, the central monitoring subsystem is often located so as to be readily available to the health care providers using the system, for example, in a hospital or doctor's office. However, since the central monitoring subsystem could be used and shared by a number of doctors and hospitals, it could be located in a remote location, accessible by modem, local area network ("LAN")/wide area network ("WAN") or the Internet, so that relevant reports could be distributed electronically to the relevant health care providers who require such reports.

In the representative embodiment, the central monitoring subsystem comprises at least one computer processor coupled to a telecommunications line by (for example) a modem capable of interpreting dual tone multifrequency (DTMF) and/or voice signals, software to control the operation of the computer processor, a database and DBMS to store information and generate reports regarding the health status of patients, and a voice generator capable of generating voice instructions understandable by humans over the telecommunications system. Optionally, the central monitoring subsystem can include a speech recognition board such as a discrete, multiword speech recognizer or speaker-independent continuous digit recognizer, and/or a printer for printing the generated reports. Further, the computer processor can be part of a LAN.

The patient subsystem enables a patient to transmit information about the patient's health status to the central monitoring subsystem. There is likely to be more than one patient being monitored at a time. Thus, in the representative embodiment, each patient will have (or have access to) a patient subsystem. Typically, the patient subsystem will be located in the home or office of the patient. It is noted, however, that (depending on the condition of the patient) the patient requires no special equipment to successfully utilize the capabilities of the present invention. The patient may use, for example, any telephone as the patient subsystem. The patient subsystem of the present invention may be a touch-tone telephone generating DTMF tones or, if the central monitoring system includes speech recognition means, a regular pulse telephone.

In the representative embodiment, the patient subsystem comprises an instrument capable of receiving instructions from the central monitoring subsystem and capable of sending data to the central monitoring subsystem. Typically, the patient subsystem comprises a touch tone telephone coupled to a telephone line. (For patients without a home telephone or traveling, a pubic telephone may be used. Alternatively, patients may use a cellular telephone as the patient subsystem.) For more sophisticated users, the patient subsystem may be a computer and modem.

Thus, in a typical embodiment of the present invention, the patient needs only a telephone. This is the same kind of telephone already owned by most households. Further, the telephone used in the present invention need not be in addition to the one used for everyday calls; nor is any additional telephone line required. (More sophisticated patients can use a computer with a modem to communicate with the central monitoring subsystem.) Thus, there will be no additional cost to the patient for special equipment. Nor does the health care provider acquire expensive equipment according to the present invention.

In a representative embodiment, the central monitoring subsystem includes a general purpose, off-the-shelf, home computer, software, a voice generator, and a DTMF modem. These components are relatively simple devices commonly available. As is known in the art, the DTMF modem is capable of receiving the dual tones generated by a touch-tone telephone keypad that have been transmitted over the telephone line and translating the tones into characters recognizable by the computer processor. The equipment used in the representative embodiment of the present invention is readily available commercially, is inexpensive, and is easy to use.

In the representative embodiment, the computer processor of the central monitoring subsystem is capable of receiving and decoding information from patients received via the DTMF modem. Patients communicate with the central monitoring subsystem using a touch tone telephone or a computer with a modem. The information received and decoded at the central monitoring subsystem is stored in the database. The computer processor makes decisions based upon the information received and other information previously stored in the database.

The representative embodiment of the present invention operates as follows: A health care provider supplies a patient with a telephone number. When dialing this number from a telephone, the patient is connected to the central monitoring subsystem. The computer processor of the central monitoring subsystem, controlled by software, sends information (for example, instructions or questions) to the patient. Typically, these instructions or questions will be communicated orally to the patient, for example, they will be generated by the voice generator. The computer processor asks the patient to identify himself or herself, for example, by entering an alphanumeric identification or patient code using the touch tone keypad. For example, the patient presses the keys corresponding to the assigned patient code on the keypad on the patient's touch-tone telephone. It is noted that there can be added security measures, such as passwords or keycodes that may also have to be entered by the patient.) The patient code is received at the central monitoring subsystem, decoded, and the patient's record is retrieved from the database.

The patient's record typically comprises information about the patient's medical condition including information previously entered by the patient using the system of the present invention. Using the information in the patient's record, the central monitoring subsystem can generate questions that the patient must respond to so that relevant information can be entered by and received from the patient.

Additionally, or in the alternative, the patient can be provided with a printed chart of questions that the patient must answer prior to calling the central monitoring subsystem. Each patient may have a chart that corresponds to that patient's individual condition. The patient fills in the answers to the questions on the chart. The patient communicates by telephone with the central monitoring subsystem and enters the patient code (and, if required, a chart code identifying the chart that the patient is using). The central monitoring subsystem will then ask the patient for each answer that the patient has entered on the chart. The patient answers using the touch tone keypad. The chart that the patient uses may be that of the type described in U.S. Pat. No. 4,346,697 entitled "Method For Treating Depression and Other Maladies By Means Of Patient-Created Symptom Graphs", which is expressly incorporated herein by reference.

Thus, in short, after the patient has entered the patient code, the central monitoring subsystem asks the patient one or more questions, which the patient answers using keys on the patient's touch-tone telephone. The patient is instructed to respond by entering information through the keypad of the telephone, such as selecting the best answer by touching its corresponding key. The computer processor of the central monitoring subsystem records and processes the patient's response. The computer processor may select the next query by consulting the database and considering the patient's response to previous questions. The central monitoring subsystem asks the patient the next question, records and processes the response, and so on. This process continues until sufficient information has been obtained from the patient, and then the central monitoring subsystem issues final instructions and terminates the call.

When each call is terminated, or at regular intervals, the central monitoring subsystem will produce reports for each of the health care providers utilizing the present invention. Typical reports that may be generated are patient status reports, reports of patients who have not entered information for a recent period and reports of patients who should be called in for an appointment, for example, due to a change in condition or because of unsatisfactory progress. In a representative embodiment, the central monitoring subsystem can quickly alert the relevant health care provider in the event of an exigency revealed in the data gathered from the patient.

Thus, based upon the reports, the health care provider can decide upon a course of action, including whether a personal consultation with the patient is necessary, whether the patient should be contacted by telephone, or whether a change in medication is needed.

The central monitoring subsystem can include an artificial intelligence expert system that intelligently questions each patient according to that patient's needs, and intelligently assists doctors in determining which patients require a physical consultation.

The database of the central monitoring subsystem can be the same database used by the health care provider to store patient records, such as name, address, billing information and the like.

In an alternative embodiment, the central monitoring subsystem can receive and interpret the patient's information in voice format. For example, the patient may be asked to identify himself or herself. Instead of or in addition to entering a patient code, the patient can speak his or her name into the telephone, which is received by the central monitoring subsystem and compared with voice fingerprints previously stored, thus providing a secure way of identifying patients.

Additionally, the present invention can be adapted so that patients can also provide information to the central monitoring subsystem by means of a computer, such as a personal computer, and modem, of the type usually found in a home. The patient can directly dial up the computer processor of the central monitoring subsystem using the modem or indirectly via the Internet, and interactively provide answers to questions communicated over the modem by the central monitoring subsystem. The questions could be presented to the patient in the format of the forms described in U.S. Pat. No. 4,346,697 referred to above.

In the representative embodiment, the patient can be charged for use of the present invention. For example, the central monitoring subsystem may only be accessible via a "1-900" telephone number, where the patient is charged a premium rate per minute of call. Alternatively, the central monitoring subsystem can record the number of calls made by the patient, and charge the patient a fixed rate per call. However, it is recognized that the present invention can be provided free of charge to patients, for example, as a service by a doctor or through other health care providers, such as HMOs or drug companies, to attract new patients or customers.

In an alternative embodiment of the present invention, automatic speech recognition ("ASR") technology is used at the central monitoring subsystem to recognize patient's verbal responses. With this additional functionality, the patient can choose to respond to the computer processor's questions using either DTMF signals or verbal responses.

In summary, the present invention provides a screening process that is significantly more efficient than the primary care systems in place today. It is less costly because it makes no demands on the time and expertise of the health-care provider for the purpose of gathering data on the health and status of patients. Rather, the provider uses his time and expertise far more effectively by analyzing the raw data that, prior to the invention, the health care provider would have had to gather manually.

The patient does not have to visit a hospital or occupy a hospital bed for regular monitoring of health status, but rather, is able to provide such information conveniently from any telephone. Needed hospital beds are made available and unnecessary office visits are avoided, saving both the patient and health care provider time and money.

The present invention can be used to report and analyze more than just the vital signs and physiological characteristics of a patient. For example, the present invention can also be used to report and analyze emotional, mental and psychological characteristics of a patient, and indications of general well being. For example, when the patient is taking medication, the present invention can be used in the treatment of depression and other maladies. It can also be used to carry out an extensive psychological evaluation of a patient on an on-going basis.

The present invention can also be used within a hospital or nursing home to obtain information from patients. Thus, for example, psychological related information can be obtained from patients at regular intervals using the hospital's or nursing home's internal telephone system.

Also, unlike the other existing systems, the present invention is adaptive. That is, it can, if required, actively decide what information is needed from a patient based upon information received from the patient. This gives the present invention a degree of flexibility and value to the physician that is superior to that afforded by other monitoring systems.

The present invention is capable of meeting the conflicting demands of providing higher quality health care at lower cost. It is easy to use, is economical, and multiplies the utility of the medical professional in the health care system by making more efficient use of time and expertise. It also reduces the cost of medical care by allowing the health care provider to regularly obtain certain information while the patient is at home. By increasing the number of inpatients who can be treated on an outpatient basis, the present invention allows hospital beds to be used more efficiently for those with more severe conditions.

DETAILED DESCRIPTION

Figure 1:
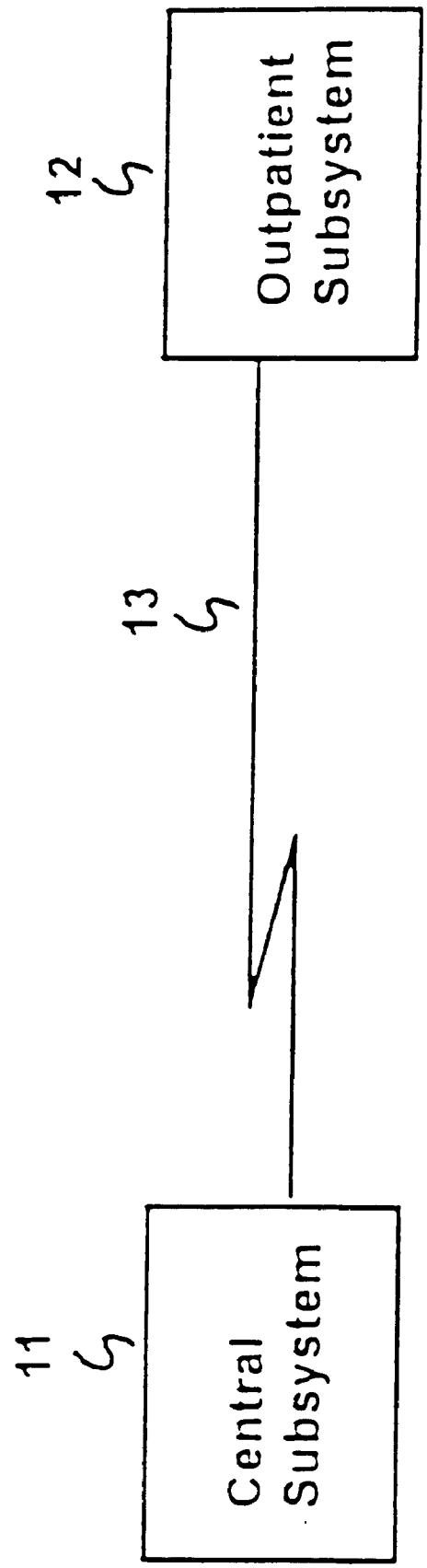
FIG. 1 is a block diagram of the two main subsystems of the present invention.

Referring now to the drawings, and initially FIG. 1, there is illustrated a representative embodiment of an outpatient monitoring system comprising two subsystems, namely, a central monitoring subsystem 11 and an outpatient subsystem 12. The central monitoring subsystem 11 is located so as to be readily accessible to one or more health care providers. The outpatient subsystem 12 is located so as to be readily accessible to an outpatient. The central monitoring subsystem 11 and the outpatient subsystem 12 are coupled by a telecommunications system 13, such as, for example, a public telephone network or the Internet.

As used herein, the term "provider" or "health care provider" includes doctors, psychologists, HMOs, hospitals, health clinics, managed care entities, drug companies and the like.

FIG. 1 shows only one outpatient subsystem 12. However, the present invention is designed for use by many patients. Thus, there will be many outpatient subsystems 12, for example, one for each patient, each coupled to the central monitoring subsystem 12 via the telecommunications system 13. There may be one or more outpatient subsystems 12, for example, at various locations around the country.

Figure 2:
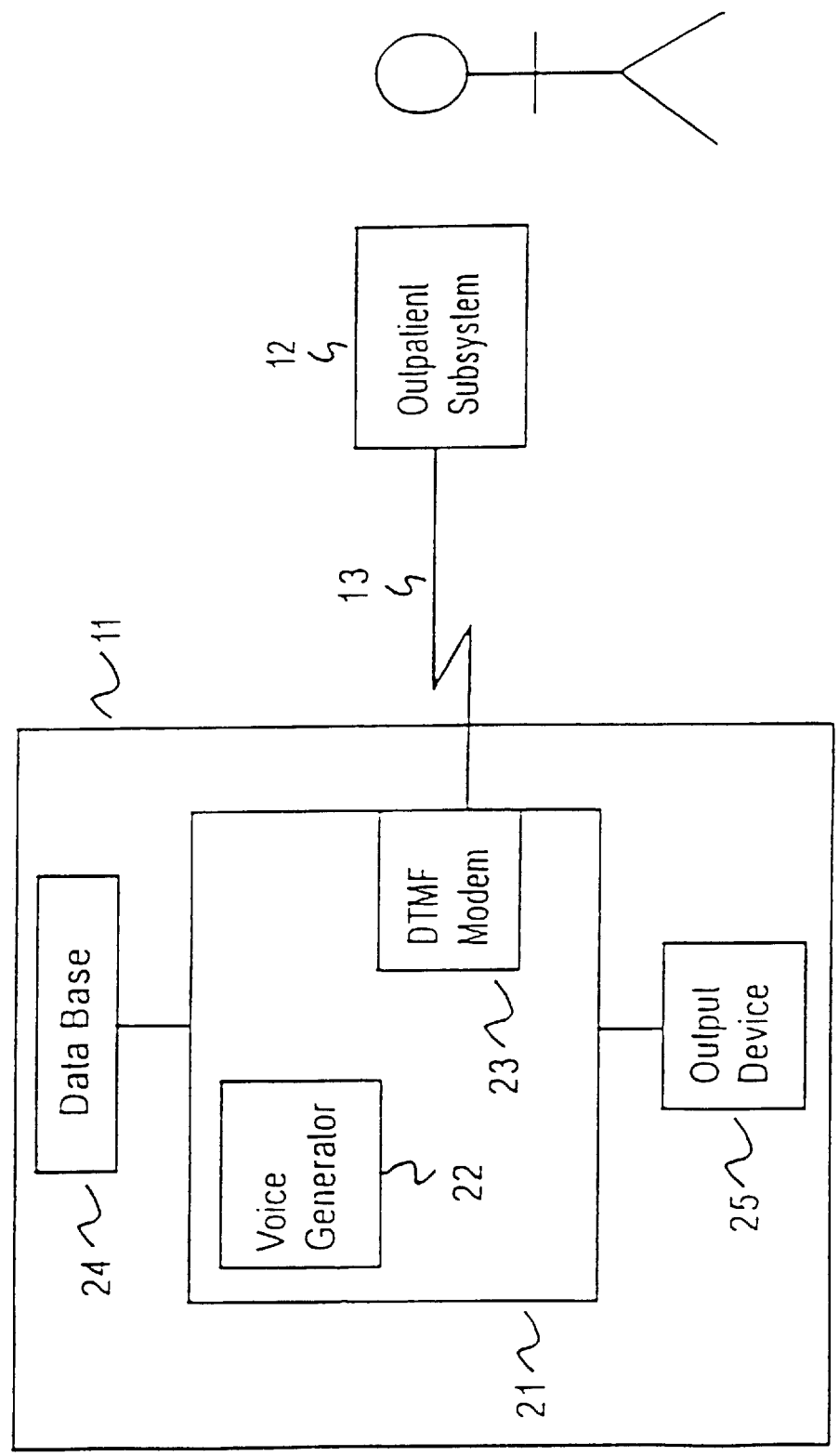
FIG. 2 is a block diagram illustrating in further detail the components of the two subsystems of FIG. 1.

Referring now to FIG. 2, the central monitoring subsystem 11 of the representative embodiment of the present invention comprises a computer processor 21, such as, for example, an Apple Macintosh computer, a SUN brand workstation or an IBM personal computer with an Intel Pentium processor. The computer processor includes (or is coupled to) a voice generator 22 and a dual tone mult ifrequency (DTMF) modem 23. The computer processor can also access a database 24, storing, for example, patient information and health status information that is input by a user, such as, for example, a patient. The computer processor 21 is also coupled to an output device 25, such as a monitor or a printer. The voice generator 22 and the DTMF modem 23 are coupled to the telecommunications system 13.

The computer processor 21 is capable of executing software programs, such as DBMS programs and other programs capable of carrying out the operations involved in patient monitoring. The computer processor 21, in conjunction with the software programs, is capable of actuating the voice generator 22, and can receive information from a patient via the DTMF modem 23.

The outpatient subsystem 12 of the representative embodiment is a telephone capable of generating DTMF signals using the keys of the telephone's keypad. These signals are transmitted to the DTMF modem 23 over a telecommunications system 13. The DTMF modem 23, in conjunction with the computer programs, decodes the DTMF signals and stores the received information in the database 24.

In the representative embodiment, the DTMF modem 23 is a ACC303800 Sportster FAX/modem or Digicom Systems Connection's +14.4 FAX/modem, both with DTMF dialers/decoders fax and modem chips.

The database 24 in the representative embodiment is a relational database that is used to keep track of all of the patient's medical information and other patient information. The database 24 has several properties:

Access to database 24 through a full screen graphical user interface ("GUI"). Providers and administrators will use this interface.

The ability for the health care provider to configure personalized GUI interface screens.

Access to database 24 through a "walkthrough" interface, for which only one question at a time is asked. The patients will use this interface.

The ability for the provider to configure personalized walkthroughs.

The ability to perform queries and reports.

The ability for the provider to customize a standard report.

Medical records can be referenced by provider and patient.

Patient data is stored in form of a patient history, so that trends can be tracked and the patient monitored over a period of time.

Security features prevent unauthorized access to or modification of records.

Figure 2A:
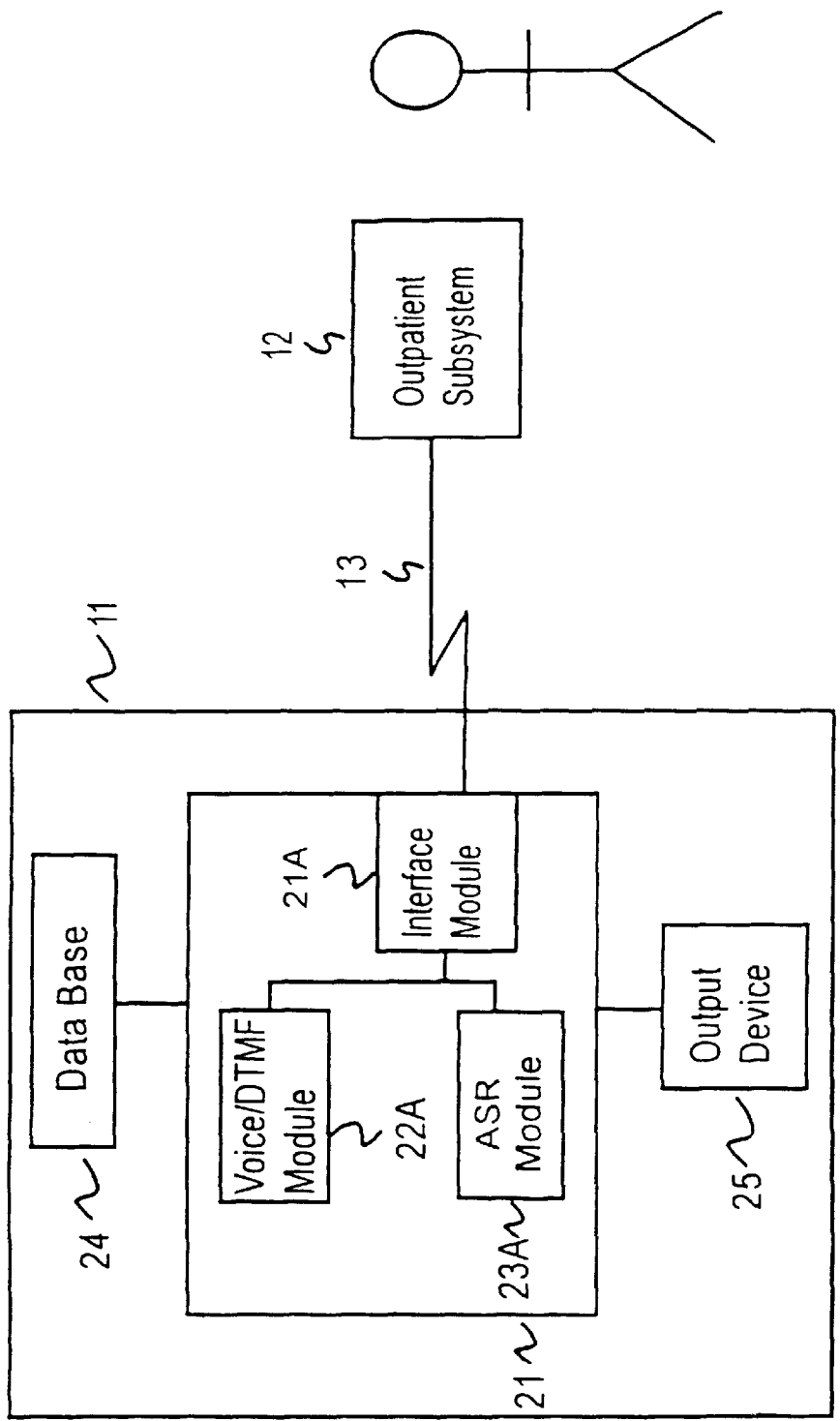
FIG. 2A is a block diagram illustrating an alternative embodiment of the components of the two subsystems of FIG. 1.

FIG. 2A represents an alternative embodiment of the present invention where an interactive voice response ("IVR") system utilizing automatic speech recognition ("ASR") allows a user to respond to the system's questions with either DTMF signals (e.g., by pressing the buttons on the telephone keypad) or verbal commands (e.g., saying a number or phrase). The central monitoring subsystem 11 of this embodiment comprises a computer processor 21 which includes (or is coupled to) an interface module 21A, a Voice/DTMF module 22A and an ASR module 23A. The computer processor can access the database 24. The computer processor 21 is also coupled to an output device 25, such as a monitor or a printer. The interface module 21A is coupled to the telecommunications system 13. The Voice/DTMF module 22A and the ASR module 23A communicate with the interface module 21A via a data bus.

As similar to that discussed above, the computer processor 21 in the alternative embodiment is capable of executing additional software programs, such as DBMS programs, speech recognition and other programs capable of carrying out the operations involved in patient monitoring. The computer processor 21, in conjunction with software programs, is capable of actuating the interface module 21A, the Voice/DTMF module 22A and the ASR module 23A and can receive information from a patient via these modules.

The outpatient subsystem 12 of this alternative embodiment is a telephone handset for transmitting the user's verbal commands. Ideally, the telephone handset also can generate DTMF signals. The patient's responses are transmitted over a telecommunications system 13 to the interface module 21A where the signals are digitized, if they are not in a digital format already, and identified as either the voice or DTMF signals. These voice and DTMF signals then are routed, via a data bus, to either the ASR module 23A for voice commands or the Voice/DTMF module 22A for DTMF signals. The Voice/DTMF module 22A in conjunction with computer programs decodes the DTMF signals and stores the received information in the database 24. The ASR module 23A in conjunction with computer programs decodes the voice signals and also stores the received information in the same database 24.

With regard to the voice signals, the ASR module 23A typically relies upon onboard microprocessors and high-speed digital signal processors ("DSPs") to perform discrete or continuous, speaker independent speech recognition. To determine the meaning of the voice signals, the DSPs compare one or more parts of a speech pattern to word template vocabularies that are downloaded to the ASR module 23A via the PC host PC-AT bus.

The speaker independent vocabulary templates are sets of words or phrases spoken by any user, which the system recognizes at a specific point in time. They can be created using a large number of samples (200–2000) from different speakers. One common 13-word vocabulary includes the words "yes," "no," the digits "zero" through "nine" and the digit "oh." A more robust vocabulary can be isolated words or short phrases (e.g., depressed, queasy, or feeling healthy). When a match is detected, the ASR module 23A communicates the results to an application program. A technique called dynamic time warping also can be used to expand or compress the duration of the speech pattern so that it can be compared to the template. Alternative speech recognition techniques include probability modeling, linguistic modeling, phonetic recognition, and neural network processing. Additional features such as allowing users to speak commands at any time during a call with no discernible effect on recognition accuracy may also be used by the central monitoring subsystem 11.

A patient's voice response can be recorded for later retrieval, for example, if a match is not detected. Also, at the end of a session, the patient may be given the opportunity to record a voice message for the health care providers.

In the alternative embodiment, the interface module 21A can be a Dialogic LSI/120 Loop Start board for use with interfacing to an analog network or a DTI/211 T-1 board or a DTI/212 E-1 board for digital networks. The Voice/DTMF module 22A can be a Dialogic D/240SC circuit board. The ASR module 23A can be either a Dialogic VR/16 16-port ASR circuit board for low-density systems, a Dialogic Antares 2000 circuit board for high-density systems, or a software-based speech recognition package like VRSoft from Voice Control Systems ("VCS") or VPro from Voice Processing Corporation, which both can used in conjunction with the Voice/DTMF module 22A. All of these circuit boards are manufactured by Dialogic Corporation, Parsippany, N.J. and are designed to be installed into an IBM PC AT (ISA bus) and compatible computers (80286, 80386, 80486, and Pentium based PC platforms).

Figure 3:
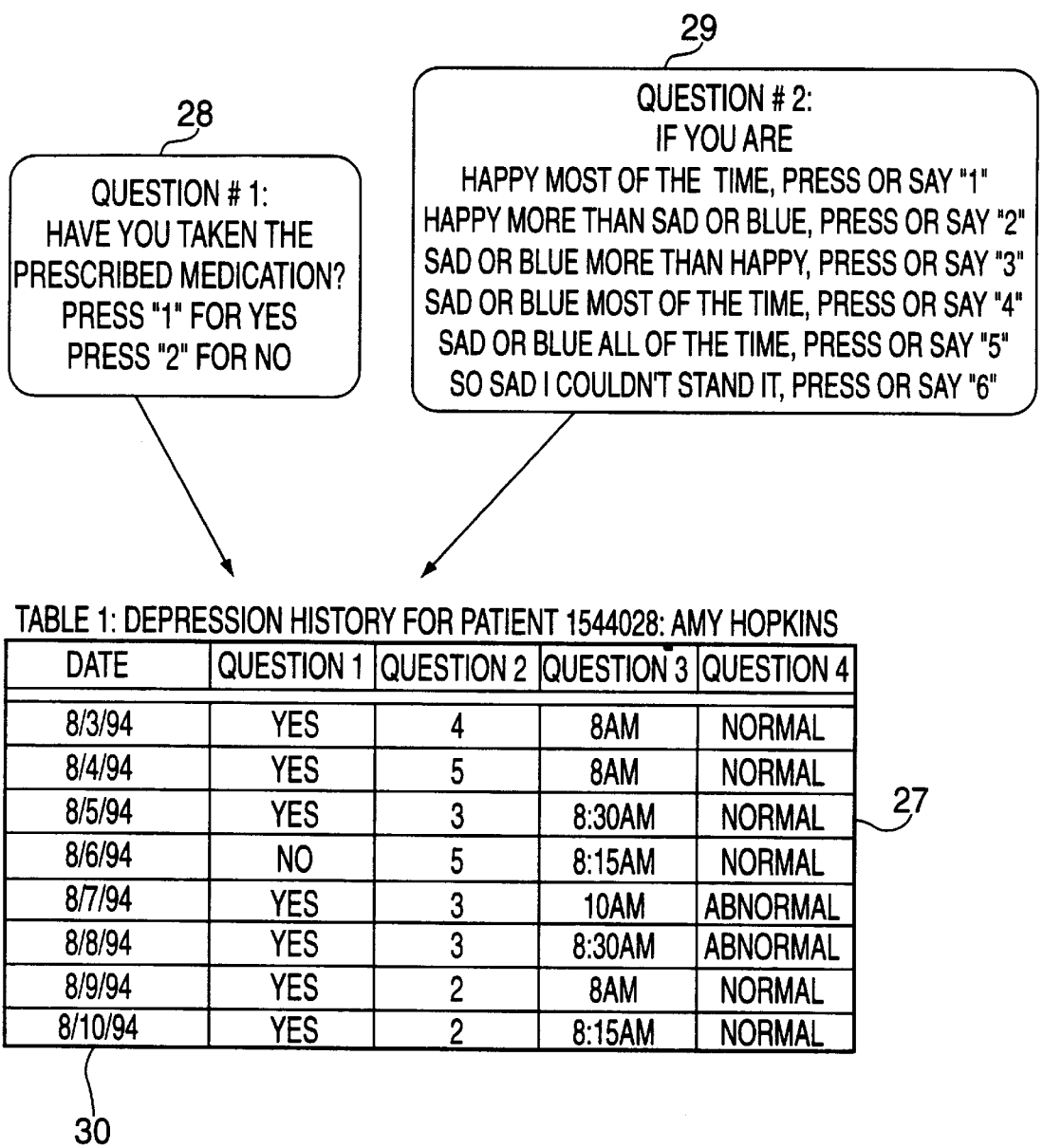
FIG. 3 is an example of a patient history, as recorded in the database of FIG. 2.

FIG. 3. illustrates a typical history table 27 for one patient. This particular patient is taking medication for depression, and has been told to phone daily to provide answers to questions. Each question is given a number. Question #1 (28) is "Have you taken the prescribed medication?". Question #2 (29) asks the patient to judge how sad or happy he or she feels. Each of these questions are asked daily, and perhaps many other questions as well. The database 24 stores this information by date, because most health care providers wish to make reports based on date. Thus ordering scheme of the database 24 is the same as the health care provider's most common requests, and generating a chronological report will not involve a huge sorting of the database 24.

The table 27 in FIG. 3 refers to a particular user, Amy Hopkins, ID number 1544028. The first column 30 specifies the date that the data was collected. The other columns list the answers to each question for the associated day. By reading down a column, you can track the history of how the answer to a question varies over the entire week Aug. 3, 1994 to Aug. 10, 1994. In the representative embodiment, each patient has a similar table, and it is possible to combine the data on several patients into a single report.

As used herein, a walkthrough is one session with a patient. In this example, a walkthrough begins when a patient starts answering questions about depression. The walkthrough ends when the patient answers the last depression question. In one embodiment of the present invention, a walkthrough flowchart defines what questions will be asked of the patient. What questions are asked depends entirely on what responses the patient gives. This is not a programming flowchart which describes how a program flows. Instead this flowchart describes how a patient walkthrough session flows.

There will be many flowcharts in the system. One may cover depression. Another may cover diabetes. Each patient will be led through the appropriate flowchart depending on their illness, in a procedure to be described later. Some patients may be led through one flowchart, and then another, if they should answer questions about more than one topic.

Figure 4:
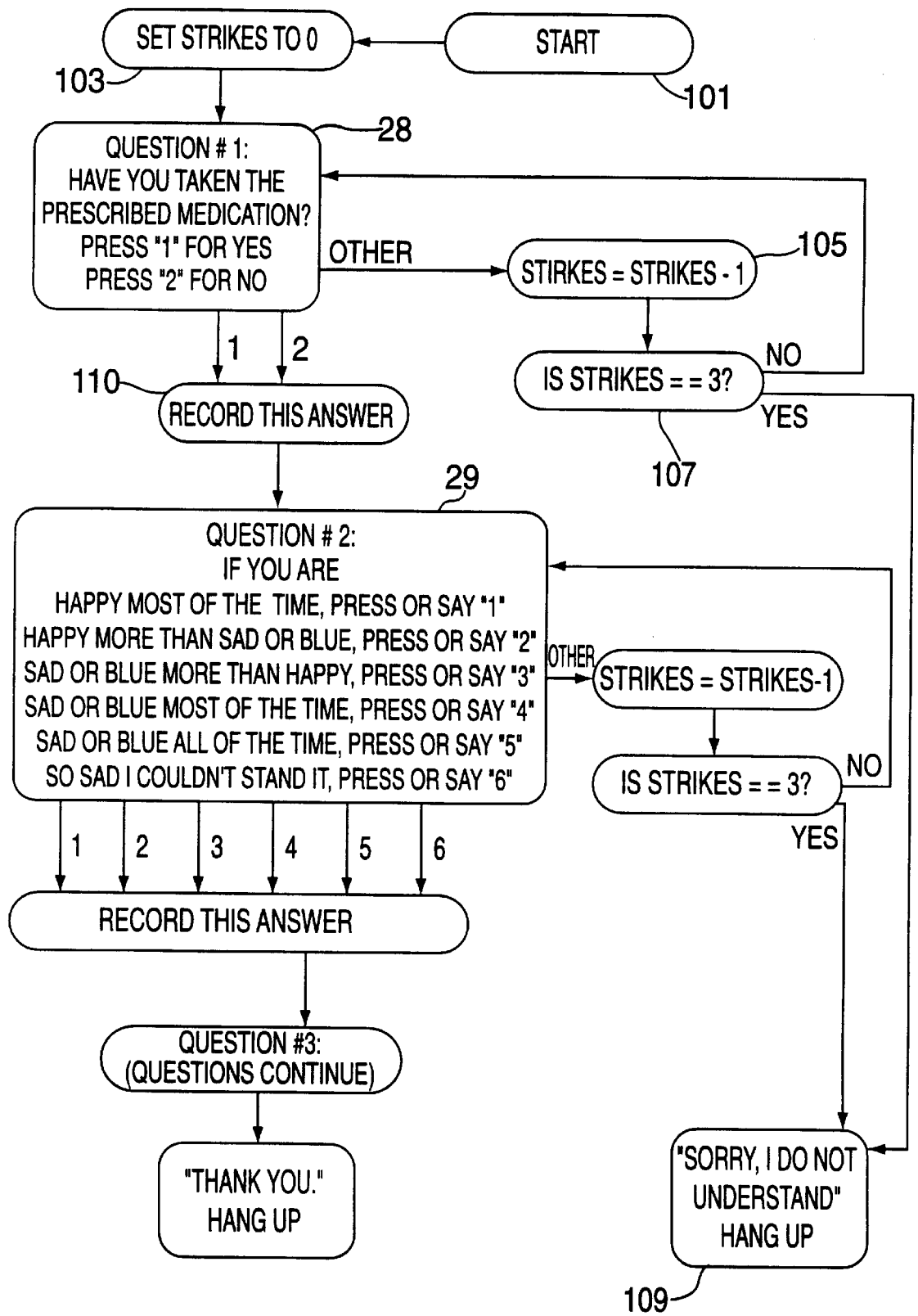
FIG. 4 is an example walkthrough flowchart.

FIG. 4 is an example of a walkthrough flowchart for depression. When the patient is to answer questions about depression, the program starts at the START cell 101. A variable called STRIKES is set (103) to keep track of the mistakes that the user has made so far. This variable will ensure that the walkthrough is completed even if the user is constantly entering bad numbers, or if some communication problem is disrupting reception.

The walkthrough can travel from one cell to another along an arrow. So after "Set Strikes to 0" (103), the next cell is the "Question #1" cell (28). The user is asked the question listed in this cell. There are several arrows leaving this cell. The arrow that is chosen is the one matching the patient's answer. For example, if the patient selects "1", then the arrow marked "1" is followed to the cell labeled "record this answer" (110), signifying that the answer is recorded in the database 24. If the patient does not respond "1" or "2", then the STRIKES variable is incremented (105), and the session may be ended if too many nonsensical answers have been given (107, 109).

The walkthrough continues to the "Question #2" cell (29), and eventually, after many more questions, to the ending of this walkthrough.

In the representative embodiment, supporting modules couple the database 24 and the walkthroughs together in application. A module is a computer programming concept that represents a piece of software that performs a small, well-defined function. A software project is constructed of several modules that use each other to accomplish a task. Sometimes, all the modules for a software project are placed together inside one program. Otherwise, the modules are placed in more than one program, and these programs must talk to each other. One benefit of placing the modules for a software project in more than one program is that each program can be run on a separate computer. The resulting parallelization is usually much faster.

Figure 5:
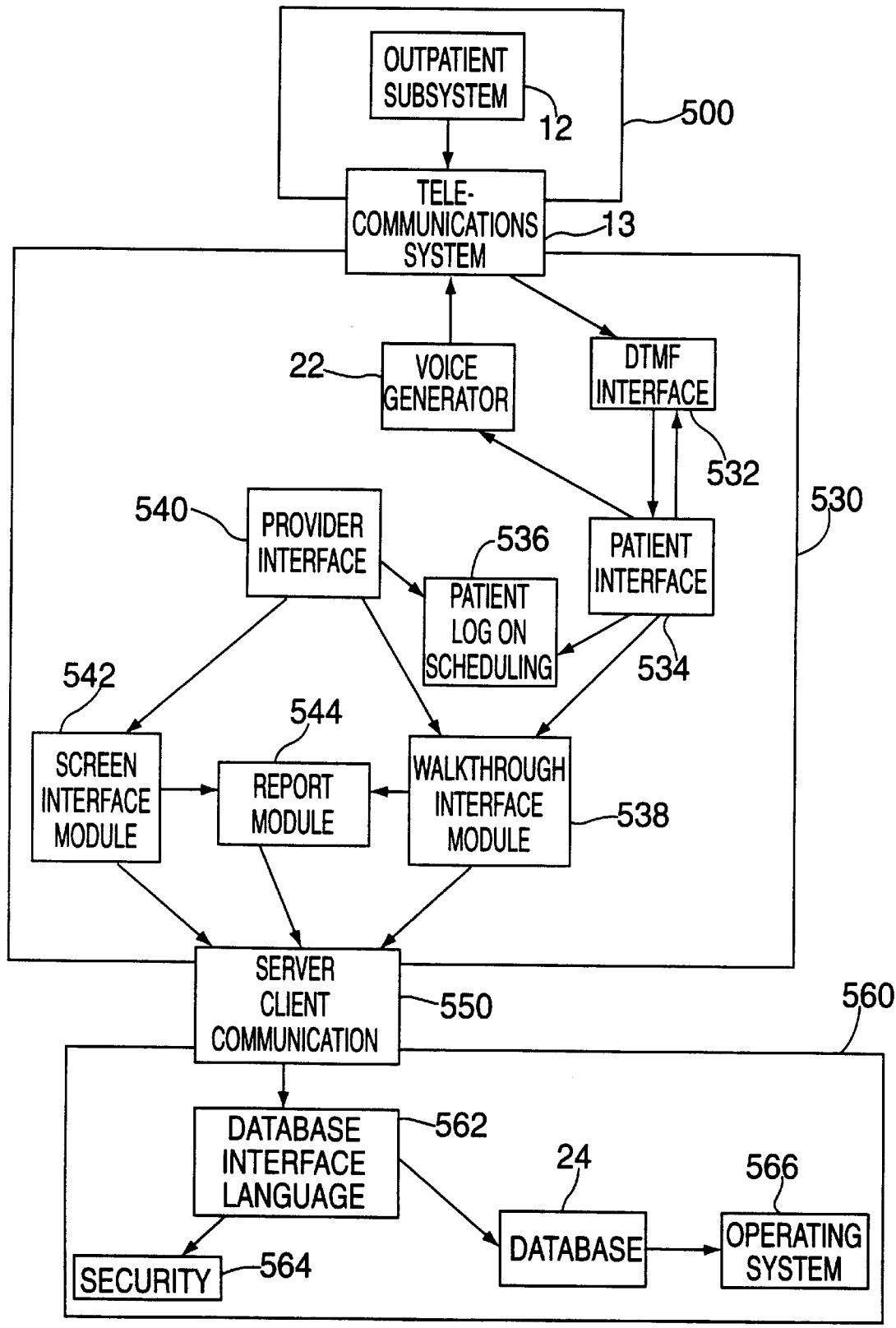
FIG. 5 is a detailed block diagram elaborating on the components of the system described in FIG. 2.

For this patient database application, there are several modules that support the functionality of the whole software project. FIG. 5 illustrates, in block diagram form, the modules used in the representative embodiment of the central monitoring subsystem 11. It is possible to describe the entire system by describing each module individually. The modules illustrated in FIG. 5 are representative only, and other configurations of modules may be used, depending on the functionality required and other design decisions.

FIG. 5 has been divided into three systems, namely, a patient system 500, an interface server 530 and a database server 560. Each system can run on a separate computer. The patient system incorporates the outpatient subsystem 12 and is coupled to a telecommunications system, as described above. The interface server 530 handles the process of getting answers from patients. It also allows access to the database 24 by the health care provider and other administrators. The database server 560 stores patient information. (The interface server 530 and the database server 560 can be regarded as comprising the central monitoring subsystem 11 of FIG. 2 above.)

Each of these separate systems can communicate over a network. For example, in the representative embodiment, the patient system 500 communicates with the interface server 530 through phone lines 13. The interface server 530 communicates with the database server through a LAN. It is also possible to combine the interface server 530 and database server 560 together into single program.

The following is a description of each module.

The outpatient system 12 is the means by which the patient communicates with the central monitoring subsystem 11, as described above. A function of the outpatient subsystem 12 is to give the patient access to the interface server 530.

The voice generator 22 speaks for the system. Whenever a question needs to be asked to the patient, the voice generator 22 translates the computer question into voice that the patient can hear.

The DTMF interface 532 alerts a patient interface 534 that a new patient has dialed in. The DTMF interface 532 picks up the phone and listens for any tones that are pressed. Any tone information is passed along to the patient interface 534. Also, the DTMF interface 532 has a timeout function, so that if the patient waits too long (perhaps 2 minutes) to press a key, it will inform the patient interface 534 that no key was pressed. This insures that the system never hangs. In a similar way, the DTMF interface 532 checks to see if the patient has hung up the phone. If this happens, it also informs the patient interface 534.

The patient interface 532 finds out who the patient is, asks the Patient Logon Scheduling to find which walkthroughs the patient must go through. It then performs each walkthrough, one step at a time, calling on the walkthrough interface module 538 to interpret each walkthrough.

The following are representative examples of the functionality performed by the patient interface module 534:

Handle Patient Dialup

This procedure is called by the DTMF module 532 to handle the entire patient call by using other modules to record the patient information.

A. Execute the walkthrough "PASSWORD" using the Execute Walkthrough Algorithm, discussed below B. Get patient ID and password confirmation from Walkthrough Interface Module 538

C. If password confirmation is given:
1. Give patient ID to Patient Logon Scheduling Module 536
2. For each walkthrough in the Patient Logon Scheduling Module:
   a. Receive next walkthrough name from Patient Logon Scheduling Module 536
   b. Execute that walkthrough using the Execute Walkthrough Algorithm In summary, the Handle Patient Dialup procedure is activated whenever a patient dials up. In Step A, the patient interface module 534 asks for the patient's password and identification number. These questions, like any other question in the system, can be described by a walkthrough, which is executed. In Step B, the patient interface module 534 receives information on whether the patient password is valid. If the password is not valid, then in Step C, not further action is taken. Otherwise, the password is valid, so in Step C1, the patient interface module 534 asks the patient logon scheduling module 536 to pass over all the walkthroughs this patient must go through. For example, in one embodiment, if the patient is depressed and a diabetic, then she must go through a walkthrough for depression and a walkthrough for diabetes. In Step C2, each walkthrough is executed in Execute Walkthrough procedure.

Execute Walkthrough

This procedure is called to let the patient walkthrough a specific information recording session. The Walkthrough Interface Module 538 supplies the questions. The patient interface 534 plays the questions with the voice generator and receives the answers with the DTMF interface 532.

A. Register this patient with the Walkthrough Interface Module 538

B. Ask the Walkthrough Interface Module 538 for questions

C. While the Walkthrough Interface Module 538 has more questions to ask:
1. Tell the voice generator 22 to say the question.
2. Tell the DTMF interface 532 to receive an answer
3. Pass the answer (which may be a timeout) to the Walkthrough Interface Module 538.

The Execute Walkthrough procedure uses a walkthrough to ask a patient all the appropriate questions. As discussed earlier, the path and questions asked can be determined by the answers the patient gives. Nonsensical answers may terminate a walkthrough. If "normal" answers are given, they are recorded in the database 24. The patient interface module 534 does not make decision about what questions to ask. This is done by the walkthrough interface module 538. The patient interface module 534 asks the walkthrough interface module 538 for Question #1. Once it gets the question, the patient interface module 534 asks the user that question through the voice generator 22, in Step C1. Then the patient provides an answer, which is read through the DTMF interface 532 in Step C2. Finally, the answer is given to the walkthrough interface module 538 in Step C3, which makes use of the answer and provides the patient interface module 534 with another question to ask.

This architecture may seem complex, but the goal is to reduce the complexity and generality of each module. This facilitate changes in modules that may be required when the system is updated or modified. In alternative embodiments, different module configurations may be used.

The patient login scheduling module 536 determines which walkthrough(s) each patient must go through. The health care provider can of course modify the schedule using a provider interface 540. Some patients go through more than one walkthrough.

The provider interface 540 is a complex GUI that makes it easy for the health care providers and administrator to access the database system. They can configure their own screens for data entry and display using a screen interface module 542. They can configure their own reports using a report module 544. They can configure walkthroughs using the walkthrough interface module 538. Of course, the system is provided with several reports, screens, and walkthrough, so many providers will not need to create any additional interface screens, reports, or walkthroughs at all.

The screen interface module 542 stores and displays GUIs to data entry and data display from the database 24. Graphical User Interfaces (GUIs) are standard to the industry, and thus need not be described in detail here. The provider interface 540 can ask for a particular screen to be displayed. It is also possible through the provider interface 540 to create new screens and modify existing ones.

The walkthrough interface module 538 controls the walkthroughs, and the patient's journey through them. The walkthrough interface module 538 gives questions to the patient interface module 534 to ask the patient, and receives answers from the patient interface module 534. In place of an answer, the walkthrough interface module 538 may receive a "no response" or "hangup" response. The walkthrough interface module 538 remembers what question was asked most recently, and thus knows or can determine, which is the next question to ask. The walkthrough interface module 538 is in charge of sending answers to the database 24 to be stored. It can also be told to print a special report by using the report module 544.

The following procedure describes part of the walkthrough interface module 538.

Handle One Question and Answer

This procedure is called by either the Provider Interface 540 or the Patient Interface 534. It goes through each step of a walkthrough, asking questions and getting answers. This procedure uses a variable "LAST QUESTION" which records the last question asked of the patient.

A. Get "answer" from the Provider Interface 540 or Patient Interface 534

B. If there is no "LAST QUESTION" then:
Set "LAST QUESTION" to question #1.
Return question #1.

C. Otherwise,
1. This data is the answer to the "LAST QUESTION"
2. a. Record the data, if appropriate.
2. b. Generate the next question for this patient, if appropriate.
3. If there is a next question for this patient:
   a. Set "LAST QUESTION" to be the next question
   b. Return this question
4. Otherwise,
   Return that no questions are left to ask The procedure "Handle One Question and Answer" receives the answer to the last question from the patient interface module 534 in Step A. Of course, there is no answer to receive if Question #1 has not been asked yet, which is the case handled in Step B. In that case, the appropriate response is to ask Question #1. This question is "remembered" so that when an answer is received, it can be matched with Question #1. If this is not the first question, then in Step C, the answer received is matched with the last question asked, stored in a variable. This answer may be recorded in the database 24, or may cause a report to be printed out. In Step C2b, a new question is generated and passed to the patient interface module 534, in Step 3.

The report module 544 performs queries on the database 24 and produces reports. Reports may be printed out for a provider to read or for record keeping. Reports may be stored on-line for future reference, or may be sent to a provider directly, for example, by email. The provider or administrator may create a new report or modify an existing report using the report module 544 through the provider interface 540.

The Server/Client Communication 550 is, in the representative embodiment, a local area network (LAN) that allows the interface server 530 to communicate with the database server 560. It is possible that these two servers are actually running on the same computer, and possibly as part of the same program, in which case there is no need for the Server/Client Communication 550.

The database 24 has an interface that is simple to understand. The Database Interface Language 562 provides a way for programmers to create queries and have them run as small interpreted programs. Database languages are standard to the state of the art in databases. The "Database Interface Language" 562 asks a Security module 564 to validate all requests.

Ideally, the database 24 forces users to identify themselves to protect the database 24 from unauthorized accesses and additions.

The database 24 actually stores the data. Because it is controlled through an easy to use "Database Interface Language" 562, the database 24 itself can be quite complex. Allowing complexity also allows the database 24 to be high performance, or distributed across several hard drives. The database 24 utilizes the computer's underlying operating system 566 to store all files.

Other modules that can be incorporated into the central monitoring subsystem 11 include a medical questions and forms file, a patient billing subsystem, a database table of health care providers, a drug database and compliance subsystem, an expert system with rules for diagnosis, treatments and alerts, and an electronic mail system.

Accordingly, the software of central monitoring system 11 of the present invention has the capability of: identifying the patient or health care provider and invoking the appropriate security checks; retrieving patient records; activating an expert system that determines what questions to ask the patient; activating the expert system to evaluate a patient's responses; if appropriate, activating drug compliance and recommendations files; making recommendations to the patient and the health care provider; recording patient usage and/or billing; and forwarding appropriate reports and alerts to the health care provider.

In an alternative embodiment, the outpatient subsystem 12 can include a personal computer coupled to the telecommunications system 13 by a modem, so as to enable modem to modem communication between a patient and the central monitoring subsystem 11. (This embodiment is particularly useful for patients having a hearing problem.)

The central monitoring subsystem 11 can be coupled to the telecommunications system 13 over a PBX (Public Branch Exchange).

The computer processor 21 can be a plurality of computer processors, such as high-end personal computers with Pentium chips, coupled together as a local area network. Preferably, there would be separate network and data servers. For example, once a patient's access code is decoded, that patient's file could be batch loaded from the data server into the local PC memory, and the PC would handle all of the interactions with the patient, freeing the network. (In fact, a single PC could handle more than one patient call simultaneously.) Some of the data stored could be stored on CD-ROM resident in each PC. The CD-ROMs could store digitized sound bytes and the PCS could use a local multimedia sound card to reply to the calling patient. This could allow, for example, the use of a simpler voice mail-type system (that often is bundled with large PBX systems) to give the patient or provider access.

Optionally, the central monitoring subsystem 11 has capabilities for: electronic mail interfaces to allow questions or queries by users; management of telecommunications ports to insure access by all users; and regular backup of patient files.

Figure 5A:
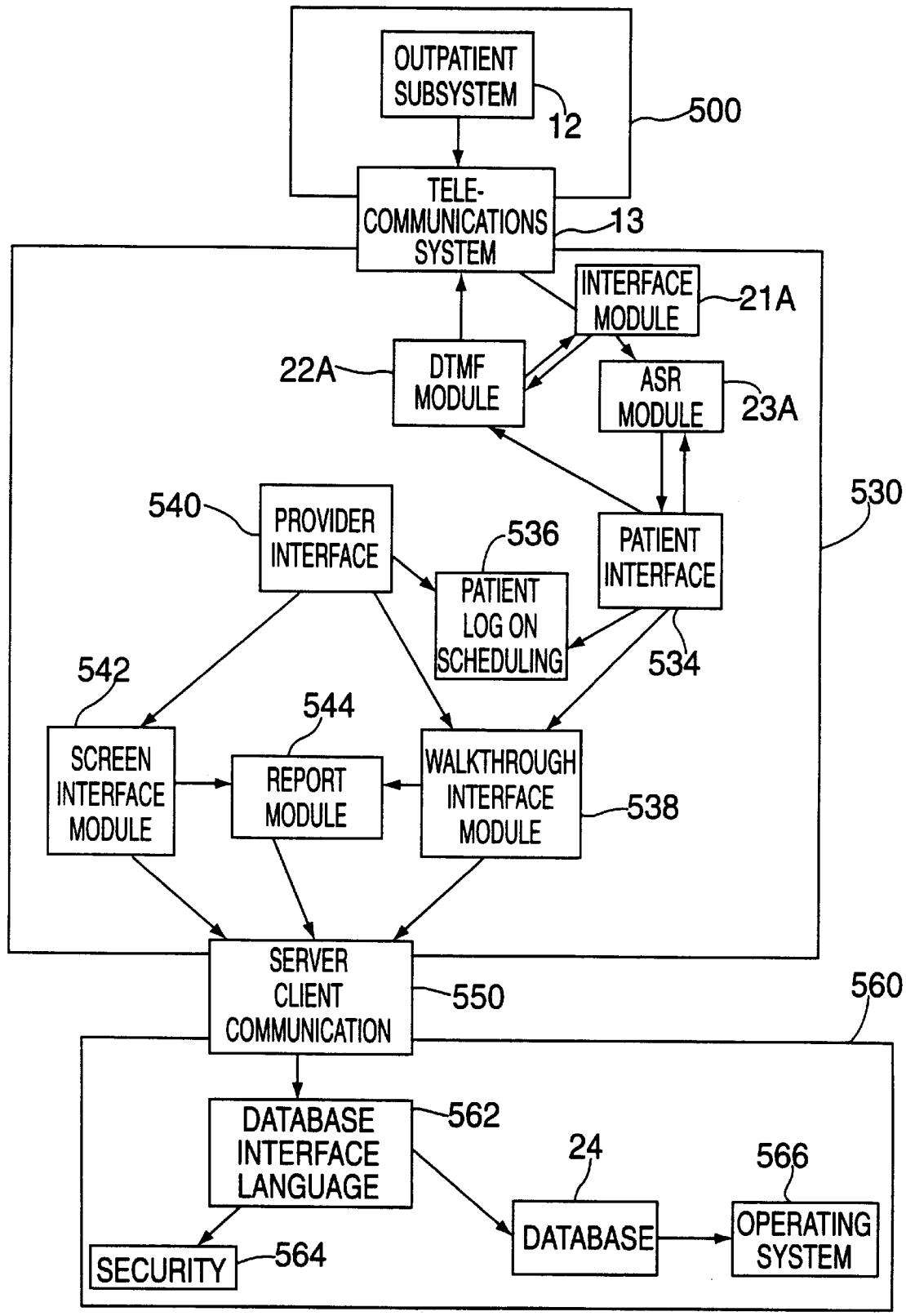
FIG. 5A is a detailed block diagram elaborating on the components of the system described in FIG. 2A.

FIG. 5A is an alternative embodiment of the present invention illustrating, three systems, namely a patient system 500, an interface server 530 and a database server 560. Interface server 530 has been modified from the FIG. 5 configuration to include speech recognition functionality. This added feature requires the DTMF interface 532 of FIG. 5 to be replaced in FIG. 5A by an interface module 21A and an ASR module 23A. Thus, for this embodiment, the term DTMF interface 532 should, where appropriate, be understood as meaning the interface module 21A and the ASR module 23A.

The Voice Generator 22 from FIG. 5 is replaced with the Voice/DTMF module 22A which alerts the patient interface 534 that a new patient has dialed in. The Voice/DTMF module 22A also picks up the telephone and listens for any DTMF signals that are pressed or voice commands that are spoken. If the patient waits too long (perhaps 1 minute) to press a button or to speak into the telephone, the Voice/DTMF module's 22A timeout feature will inform the patient interface 534 that no key was pressed or voice command spoken. This procedure ensures that the system never hangs. In a similar way, the Voice/DTMF module 22A checks to see if the patient has hung up the phone. If the patient has hung up the phone, the Voice/DTMF module 22A informs the patient interface 534. Furthermore, any DTMF signals from the interface module 21A are processed by the Voice/DTMF module 22A and the decoded information is forwarded to the patient interface 534.

The ASR module 23A receives all voice signals from the interface module 21A receives from the telecommunications system 13. These voice signals are then processed to determine whether the voice command matches one of the word vocabulary templates. Should the ASR module 23A determine that such appropriate voice information exists, the decoded voice information is passed along to the patient interface 534.

The present invention can be configured (a) to process DTMF only input from a patient; or (b) to only process voice input from a patient; or (c) to process both DTMF and voice input, and distinguish between such inputs; or (d) to receive information from a patient in electronic form, computer-to-computer; or (e) combinations of the above.

Figure 6:
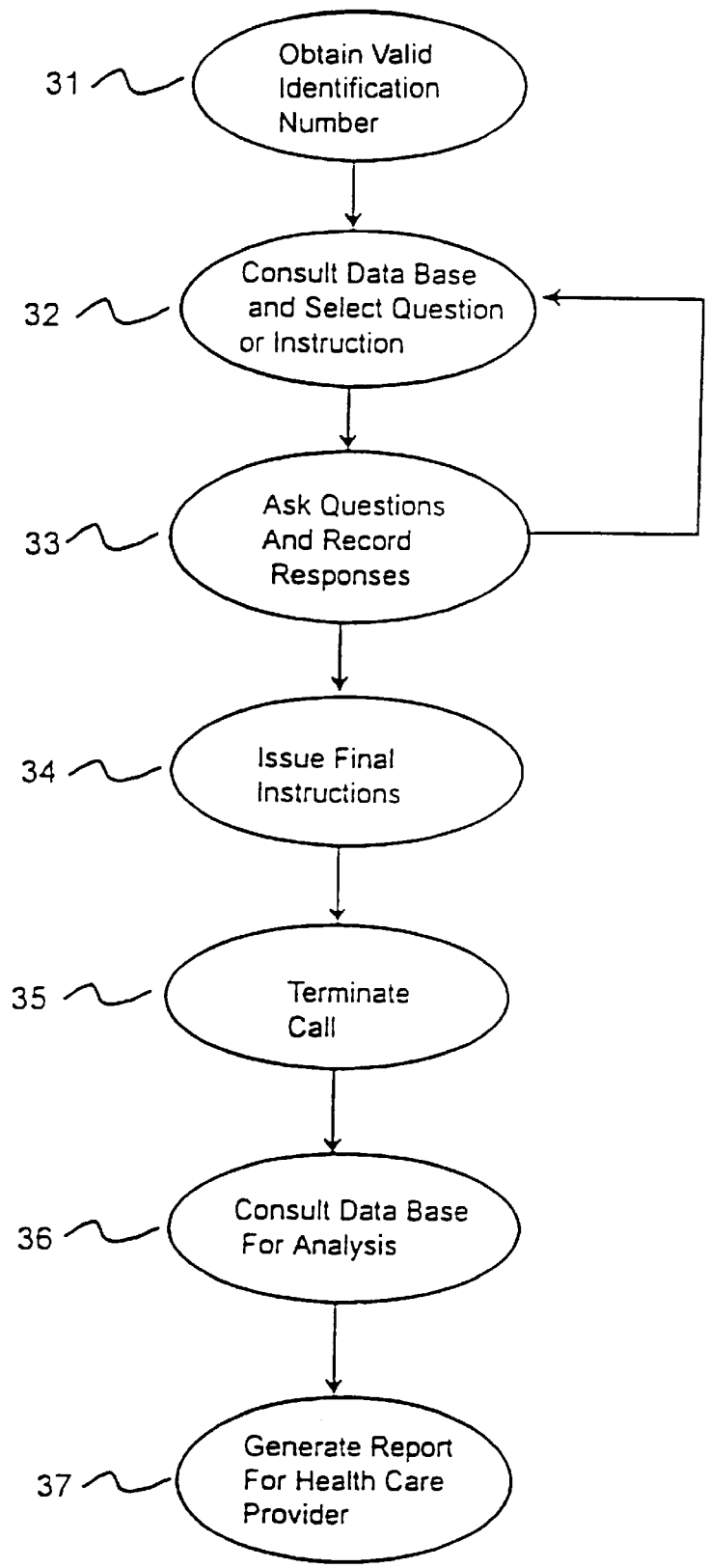
FIG. 6 is a diagram in flow chart form of a method of operating a representative embodiment of the present invention.

FIG. 6 describes in flow chart form typical steps used in the operation of a representative embodiment of the present invention. A patient utilizes the invention by dialing a telephone number supplied by the health care provider using a touch tone telephone. The modem 23 is coupled to a telephone line. (There may be more than one modem coupled to the processor 21, allowing more than one call to be handled at the same time.)

The modem 23 answers the incoming telephone call and, under the control of the computer processor and utilizing the voice generator 22, directs the patient to enter his or her personal identification number ("PIN") using the appropriate keys on the telephone keypad of the patient's telephone. The modem 23 decodes the information received from the patient, and passes this information to the computer processor 21 (step 31). The computer processor 21, after checking the database 24 to determine if the entered PIN is valid, retrieves the correct patient record.

If the PIN is not entered correctly, the computer processor 21 requests the patient to retry entering the PIN. If the computer processor 21 is unable to recognize a valid PIN after a predetermined number of consecutive failed attempts by the patient, the computer processor 21 terminates the call.

Upon accepting a valid PIN, the computer processor 21 consults the retrieved patient record and the database 24 to select one or more appropriate questions for the patient to respond to (step 32).

The computer processor 21, via the voice generator 22 and the modem 23, proceeds to ask the patient a question and instructs the patient how to transmit an answer. The patient transmits an answer, and the DTMF modem 23 translates the answer into a form recognizable by the computer processor 21 (step 33). The answer received from the patient can be stored in that patient's record in the database.

The computer processor 21 will select the next question, if any, for example by consulting the database 24 along with the patient's response to a prior question or questions. If the computer processor 21 decides that no further questioning is necessary, it will issue final instructions (step 34), if any, to the patient and then terminate the call (step 35).

After the call is terminated, the computer processor 21 will consult the database 24 (step 36), and immediately or at predetermined intervals, generate one or more reports for the health care provider (step 37). The reports are based on the patient's record in the database 24, including the answers to the questions received from the patient at the central monitoring subsystem 11. Typically, the reports are generated at the output device 25.

Figure 6A:
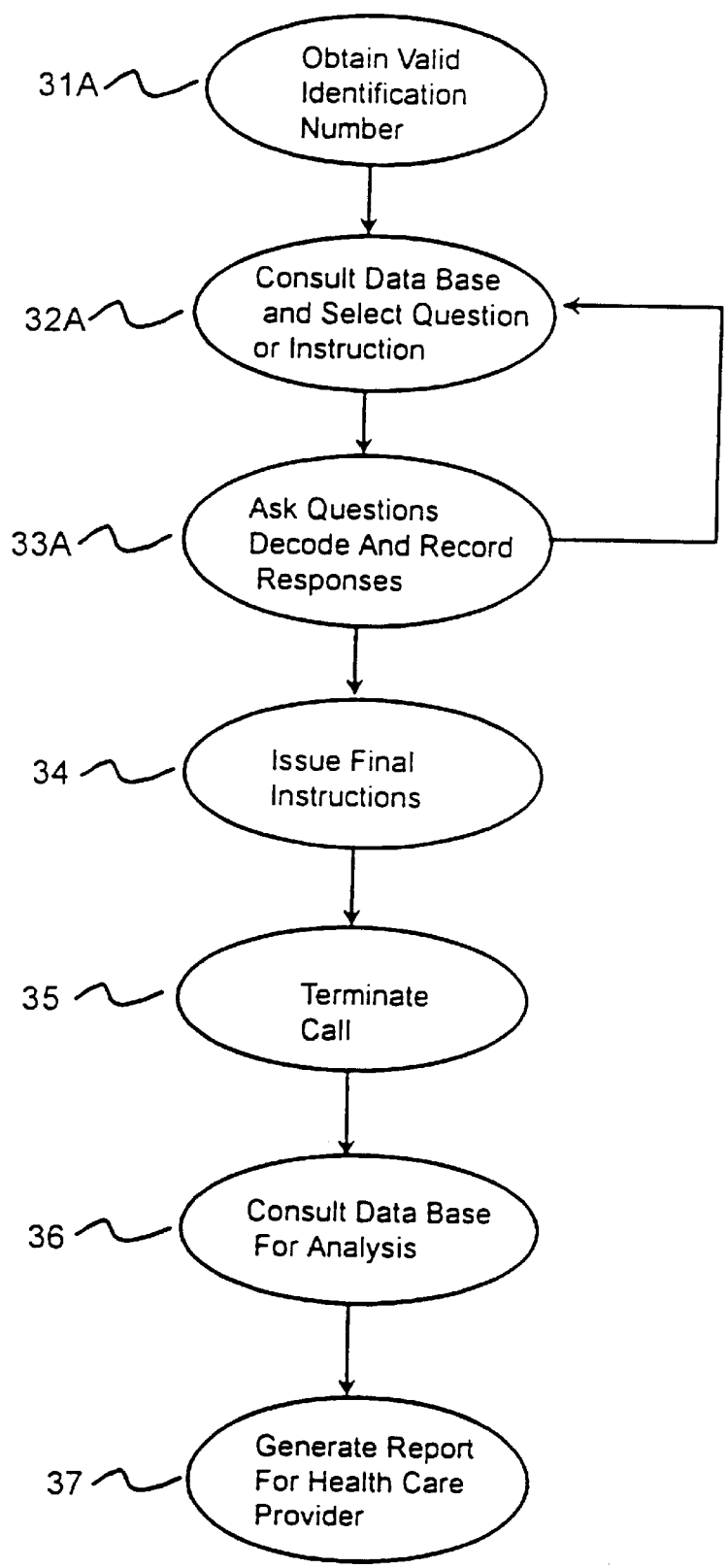
FIG. 6A is a diagram in flow chart form of a method of operating an alternative embodiment of the present invention.

FIG. 6A describes, in flow chart form, typical steps used in the operation of the alternative embodiment of the present invention having ASR technology. A patient utilizes the invention by dialing a telephone number supplied by the health care provider using a telephone. The interface module 21A is coupled to a telecommunications system 13. (The interface module 21A can allow more than one call to be handled at the same time).

The interface module 21A answers the incoming telephone call and, under the control of the computer processor 21 and utilizing the Voice/DTMF module 22A and the ASR module 23A, directs the patient to enter his or her personal identification number ("PIN") by either pressing the appropriate keys on the telephone keypad of the patient's telephone or saying certain voice commands. The interface module 21A ensures that all DTMF and voice signals are digitized and the Voice/DTMF module 22A and the ASR module 23A decode the respective DTMF and voice signals before passing the decoded information to the computer processor 21 (step 31A). The computer processor 21, after checking the database 24 to determine if the entered PIN is valid, retrieves the correct patient record.

If the PIN is not entered correctly, the computer processor 21 in conjunction with the Voice/DTMF module 22A requests the patient to retry submission of the PIN. If the computer processor 21 is unable to recognize a valid PIN after a predetermined number of consecutive failed attempts by the patient, the computer processor 21 in conjunction with the Voice/DTMF module 22A terminates the call.

Upon accepting a valid PIN, the computer processor 21 consults the retrieved patient record and the database 24 to select one or more appropriate questions for the patient to respond to (step 32A).

The computer processor 21, via the Voice/DTMF module 22A and the interface module 21A, proceeds to ask the patient a question and instructs the patient to transmit an answer by either pressing a number or saying a number or phrase. The Voice/DTMF module 22A and/or ASR module 23A translates the patient's answer into a form recognizable by the computer processor 21 (step 33A). The answer received from the patient can be stored in that patient's record in the database.

The remaining steps 34–37 are the same as those steps discussed in FIG. 6.

Attached hereto as Appendix A, and expressly incorporated herein, is pseudo-code illustrating a representative algorithm that can be used to control the operation of the computer processor 21 of the present invention.

The present invention can be used to monitor a patient's health condition whilst undergoing treatment and to monitor the health of people who have (or who are susceptible to) certain medical conditions, such as, for example, prostrate cancer, heart disease or arthritis. Accordingly, the system of the present invention can be used to monitor patients with chronic diseases, such as, for example, post MI, cancer, arthritis, diabetes, and the like. The monitoring can be of a patient's subjective and emotional state (e.g., how the patient "feels") and of the patient's physical condition (e.g., blood glucose levels).

The present invention can also be used to assist in the diagnosis of medical conditions as well as for monitoring treatment. Thus, the present invention can be used to monitor the health status of a healthy person, so that if there is a change in that person's condition, a doctor or other health professional will be alerted by the central monitoring subsystem 11. Moreover, the information entered by the person at the outpatient subsystem 12 and stored at the central monitoring subsystem 11 can be used to assist in the diagnosis of the medical condition or illness.

The present invention can be used to monitor and report side effects of drugs prescribed to a patient. When the health care provider determines, based upon the information entered by the patient and stored in the patient's record in the database 24, that the patient is being adversely affected by a prescribed drug, the health care provider can contact the patient (or have the central monitoring subsystem 11 alert the patient on the patient's next call or call the patient back) and reduce the dose of the medication or change the medication to reduce the side effect.

Another use of the present invention is to monitor patient compliance. Often when a patient is prescribed a drug, the patient does not complete the full course of treatment, fails to take the required dose at the required time, or fails to take the drug at all. Using the system of the present invention, a health care provider or drug company can monitor whether the patient is taking the required dose of a drug at the correct times. The system of the present invention can be configured so that a patient reports regularly (for example, each day) as to the amount and time that a particular drug was taken. Additionally, the central monitoring subsystem 11 can remind a patient when a patient calls of the need to take the correct dosage at the correct time, of what the correct dosage is, the conditions under which the drug should be taken (e.g., with milk, before food etc.), the side effects (e.g., drowsiness, so do not drive etc.) and the benefits of taking the drug. In an advanced embodiment, the central monitoring subsystem 11 can itself call the patient if the patient has not reported within a set period of time and remind the patient (using the voice generator 22) of the need and benefits of taking the prescribed drug.

Reporting of patient compliance with respect to the taking of drugs using the system of the present invention has many advantages. The patient is constantly reminded of the need to take the drug, and when making a report to the central monitoring subsystem 11, is educated on an on-going basis as to, for example, the advantages of the drug and the proper way to take the drug. Additionally, this compliance feature can be is used in conjunction with the patient reporting (as discussed above) as to the side effects of the drug and as to the patient's physical and mental condition whilst taking the drug. The health care provider is thus kept informed as to the patient's progress, both as to health and compliance. Moreover, the information entered by the many patients who are prescribed a drug (compliance, health status, side effects, etc.) creates an extremely valuable database of information for pharmaceutical companies, for example, as to the positive and negative effects of the drug, the time to recovery, patient outcomes and the overall success of the medication. Thus, the database 24 can also be used to store outcome information relating to one or more drugs. This information can be stored separately from the patient records.

Additionally, the present invention can be used to monitor the interactions between drugs, for example, when a patient is taking two or more drugs.

The patient record created using the monitoring system of the present invention is updated at regular intervals by the patient. This patient record, which is stored in the database 23, is an excellent record that a doctor or health care provider can use when performing a diagnosis. For example, when a doctor is examining a patient, it is usually important to take a medical history of the patient. The doctor will often ask the patient how he or she feels and how he or she felt in the past one or two weeks. Most patients cannot remember when and how they felt on particular days in the past, and what the exact symptoms they were suffering from were at any particular time. If a person uses the system of the present invention to report regularly to the central monitoring subsystem 11, a doctor will have a continuous record (created contemporaneously by the patient) of the patient's condition at regular periods in the past. This record is extremely helpful in diagnosis.

The present invention can be used for screening purposes by a health care provider. The information entered by a patient can be analyzed by the health care provider to determine which patients have chronic or acute conditions that require an immediate personal consultation.

The present invention can also be used to allow patients to make an appointment with the health care provider.

An important part of health is diet. The present invention can be used to monitor a patient's diet. For example, the patient can call in using the outpatient monitoring subsystem 12, such as, for example, a telephone, and answer questions provided by the central monitoring subsystem 11 as to what and how much the patient has eaten that day. The central monitoring subsystem 11 can then calculate and inform the patient as to the number of calories that patient has consumed. The patient can be informed by the central monitoring subsystem 11 as to the best food groups to eat, and of suggested modifications to diet. This aspect of the present invention is particularly useful for people trying to lose weight.

Many people do not live close to a health care provider. The present invention can be used to monitor the health of people living in rural areas. Also, the present invention can be used to monitor the health of under-served poor who find it difficult to visit a doctor regularly, but who have easy access to a telephone.

Thus, it will be appreciated that the present invention is a patient initiated system where the patient determines when to communicate with the central monitoring subsystem 11. The patient can determine the time at which and place from which the patient wishes to initiate the session, allowing patients on vacation or without telephones or computers to call in from public telephones. A monitoring session can be regarded as initiated by the patient when calling the central monitoring subsystem 11 and terminating at the end of that call. In one embodiment, the monitoring session is exclusively initiated by the patient. The central monitoring subsystem 11 passively waits until the patient decides to initiate a monitoring session and does not initiate or attempt to initiate contact with the patient.

For certain medical conditions, it is suggested that patients use the system of the present invention in between regular visits to the health care provider. In certain circumstances, the patient may not be truthful when answering questions according to the system of the present invention. Accordingly, a health care provider should be careful in recommending a change in medication based solely upon a patient's report to the central monitoring subsystem. In a representative embodiment, the expert system that is utilized by the present invention has functionality to help ascertain if a patient is answering questions truthfully and consistently.

When children or other family members are sick, the present invention can be used by the child's parents or other family members. For example, the mother can sit down with the sick child and ask the child questions that are printed on a chart, such as the chart described in U.S. Pat. No. 4,346,697. The mother can then telephone the central monitoring subsystem 11 and report the child's health condition.

The present invention has the capability of providing messages to patients in different languages, such as, for example, Spanish or French. Different telephone numbers could be allocated to patients who understand different languages so that the central monitoring subsystem will "know" in which language to provide messages to the patient. Alternatively, the patient could be given the option, when first connecting with the central monitoring subsystem, of changing the language of the messages.

The principles of the present invention can be used to also monitor the health and welfare of family pets and farm animals.

EXAMPLE ONE

An outpatient measures his body temperature and blood pressure at home and then uses a touch tone telephone to call a central monitoring subsystem 11 that is located in a hospital. Once connected, the computer processor 21 of the central monitoring subsystem 11 actuates the voice generator 22 and asks the outpatient to enter a PIN. Accordingly, the outpatient enters his PIN, e.g., "234165" by either using the keys of his telephone keypad or verbally repeating the numbers.

Once the identification number is accepted, the computer processor 21 asks the patient to enter the outpatient's body temperature either by pressing the touch tone keypad or by verbal command. Assuming the temperature of the patient is 98 degrees, the outpatient either presses or says "nine"; then presses or says "eight". By so doing, the outpatient tells the computer processor 21 that the outpatient has measured the outpatient's body temperature to be 98 degrees Fahrenheit.

The computer processor 21, actuating the voice generator 22, asks the outpatient if the outpatient intended to enter a body temperature of 98 degrees Fahrenheit. The computer processor 21 instructs the outpatient to press or say "one" if the answer is yes, and "two" if the answer is no. If the outpatient presses or says "one", the computer processor 21 records the 98 in the database 24 as the patient's temperature on that day at that time, and proceeds to the next question.

The computer processor 21 next asks the outpatient to enter the outpatient's systolic blood pressure on the outpatient's telephone. The outpatient presses or says "one", then "two", and then "five". The computer processor 21 confirms that the outpatient intended to enter one hundred twenty five as a systolic blood pressure and enters the number in the database 24.

The computer processor 21 asks the outpatient to enter the outpatient's diastolic blood pressure on the outpatient's touch tone keypad. The outpatient touches the keys "seven" and then "zero". The computer processor 21 confirms that the outpatient intended to enter seventy five as a systolic blood pressure and records the number in the database 24.

The computer processor may ask other questions as may be necessary. For example, the outpatient may be asked to enter information relating to mood, how well the patient slept, appetite, energy, enjoyment of the day and the like. It is noted that the present invention can be used to monitor the general health of people who are not currently undergoing treatment.

The computer processor 21 can record additional information in a database 24, such as the time and date of the telephone call.

The computer processor 21 can, using the DBMS program, query the database 24 and analyze the information received. Assume that the health care provider entered information in the database 24 at an earlier date pertaining to the outpatient. The information indicates that the outpatient's medication should be discontinued if the outpatient's systolic blood pressure falls below one hundred thirty, but only if the outpatient's body temperature is less than one hundred degrees at the same time. Further, the information indicates that the health care provider be informed of the occurrence of these conditions.

Thus, a report is generated so that the health care provider is altered to this fact, and can make a decision as to whether to telephone the patient regarding his medication or whether the patient should come in for an appointment.

Alternatively, the present invention can be configured so the voice generator 22, under the control of the computer processor 21, instructs the outpatient to stop taking his medication and terminates the call. In such a case, the computer processor 21 generates a report using the output device 25 detailing the time and date of the call, the patient's body temperature and blood pressure, and the instructions delivered to the patient. The computer processor 21 can mark the report "URGENT-READ BY [Time] [Date]".

EXAMPLE TWO

The patient may be afflicted by maladies and, in particular, by depression. The patient is provided with a symptom chart of the type described in U.S. Pat. No. 4,346,697. Upon completion of the symptom chart for a specific period, the patient is instructed to call by telephone the physician's telephone number that will connect the patient's telephone to the central monitoring subsystem 11. The patient enters his PIN by using either the keys of the touch tone keypad or verbal commands, and will respond to the predetermined questions on his chart regarding his condition during this period of time. The following is an example of the questions that the central monitoring subsystem 11 asks the patient to respond as follows:

---

A. MEDICATION:
Patient is asked if he/she has taken prescribed medication. If answer is YES, press or say the number "1"; if answer is NO, press or say the number "1" (Alternatively, the system may be configured so that the patient is instructed just to say "1" or say "2", or alternatively, just to say "yes" or say "no") .)
B. MY MOOD TODAY:
Patient is prompted . . . If you are
    Happy most of the time, Press or say "1" (or say
        "mostly happy")
    Happy more than sad or blue, Press or say "2" (or
        say "happy more than sad")
    Sad or blue more than happy, Press or say "3" (or
        say "sad more than happy")
    Sad or blue most of the time, Press or say "4" (or
        say "mostly sad")
    Sad or blue all of the time, Press or say "5" (or
        say "sad all of the time")
    So sad I couldn't stand it, Press or say "6" (or say
        "so sad I couldn't stand it")
Alternatively, the system may be configured so that the patient is instructed just to say "most happy" "sad more than happy" etc.
C. MY FEELINGS OF ANXIETY TODAY:
Patient is prompted . . . If you are
    Not anxious, tense or fearful, Press or say "1" (or
        say "not anxious")
    Occasionally anxious, tense or fearful, Press or say
        "2" (or say "occasionally anxious")
    Very anxious, shaky, or jittery inside, Press or say
        "3" (or say "very jittery")
    Very anxious, tense, or fearful most of the day,
        Press or say "4" (or say "very fearful")
    So anxious, my hands or legs were actually shaking,
        Press or say "5" (say "anxious and shaking")
    Terrified or panicky most of the day, Press or say
        "6" (or say "terrified")
(Patient continues responding to the remaining sections D through I).
J. Deals with other specific symptoms that may have occurred during this same period of time. For example, Patient is prompted . . . If you
    Fell down, Press or say "1" (or say "fell down)
    Felt faint, Press or say "2" (or say "felt faint")
    Unsteady walking, Press or say "3" (or say
"unsteady")
    Trouble urinating, Press or say "4" (or say "trouble urinating"). . . and so on through seven additional symptoms.

---

APPENDIX A (A11) Receive call from patient
(A12) Ask patient for valid identification number
(A13) Record valid identification number p
(A14) Set integer m = 1   /* m is an index for counting
                            the current number of invalid
                            responses given by the patient
                            */
(A15) While (invalid number entered and m < n) do
       /* n is a preset maximum for invalid responses,
       after which the call will be terminated */
(A16)     Ask patient for valid identification number
(A17)     If (number is valid)
(A18)       Record valid identification number p
(A19)     End if
(A20)       Increment m
(A21) End while
(A22) If (m = n)
(A23)     Terminate call
(A24) End if
(A25) set integer 1 = 0   /* 1 is a flag returned by
                          subroutine NextQuestion; when
                          1=0, there is another question
                          to be asked. When 1=1, there
                          are no more questions to be
                          asked. */
(A26) while (1 = 0) do
(A27)   FirstQuestion(p,j)     /* FirstQuestion is a
                          subroutine that imports
                          valid patient
                          identification number p and
                          exports first question
                          number j */
(A28) Ask question number j   /* j is an integer
                                  corresponding to a
                                  question stored in a
                                  database that can be
                                  asked of a patient */
(A29) Give response options
(A30) Receive response r
(A31) Set integer m = 1
(A32) While ((response is not a valid option) and (m < n)) do
(A33)     Indicate invalid choice
(A34)     Re-ask question
(A35)     Give response options
(A36)     Receive response r
(A37)       Increment m
(A38)     End while
(A39)   If (m = n)
(A40)     Terminate call
(A41)   End if
(A42)   Write Record(j,r)
(A43)   Call NextQuestion(j,r,k,l)
       /* NextQuestion is a subroutine that imports the
       current question number (j) along with the response
       given by the patient (r). The subroutine selects
       the next question k based upon j and r, and exports
       integer k to the main program. When there are no
       further questions, the subroutine sets flag 1=1 and
       exports it to the main program, which terminates the
       call. */
(A44)     set integer j = k
(A45) End While
(A46) Deliver final instructions or message to patient
(A47) Terminate call
(A48) Call ReportMaker(Record(x,y))
       /* ReportMaker is a subroutine that imports the
       questions asked along with their answers and
       generates a report for the health care provider */
(A49) Await the next call

---

What is claimed is:

1. A central monitoring system for monitoring a patient's health condition comprising:

means for identifying a patient who initiates a monitoring session;

means for retrieving a patient record from a database, said patient record corresponding to the patient who initiates the monitoring session;

means for activating an expert system that determines questions to ask the patient;

means for communicating said questions to the patient and receiving responses thereto;

means for activating the expert system to evaluate patient responses to said questions; and means for making health care recommendations to the patient means for automatically communicating health care status reports to a health care provider to enable the health care provider to make a diagnosis of the patient's health condition.

2. The system of claim 1 further comprising means for recording patient usage for billing purposes.

3. The system of claim 1 further comprising means for making recommendations to a health care provider.

4. The system of claim 3 further comprising means for alerting the health care provider if predetermined conditions are detected.

5. The system of claim 1 further comprising means for alerting the health care provider if predetermined conditions are detected.

6. The system of claim 1 wherein the means for communicating further comprises means for decoding DTMF signals received from the patient.

7. The system of claim 1 wherein the means for communicating further comprises means for decoding voice responses received from the patient.

8. The system of claim 1 wherein the means for communicating further comprises means for detecting whether a patient response is a DTMF signal or a voice response.

9. The system of claim 8 wherein the means for communicating further comprises means for decoding DTMF signals received from the patient and means for decoding voice responses received from the patient.

10. The system of claim 1 wherein the means for communicating further comprises computer-to-computer communications with the patient.

11. A central monitoring system for monitoring drug usage by a patient comprising:

means for identifying a patient who initiates a monitoring session;

means for retrieving a patient record from a database, said patient record corresponding to the patient who initiates the monitoring session;

means for activating an expert system that determines questions to ask the patient relating to drug usage and side effects;

means for communicating said questions to the patient and receiving responses thereto; and means for evaluating patient responses to said questions; and means for automatically communicating health care status reports relating to the patient's drug usage to a health care provider.

12. The system of claim 11 further comprising means for aggregating responses from a plurality of patients and providing said aggregated information to a drug company.

13. A computer-based method to report health status of a patient to a computerized central monitoring system, the central monitoring system including a computer processor, the method comprising the steps of:

remotely accessing the central monitoring system with a telephone;

at the central monitoring system, retrieving a record for the patient;

at the central monitoring system, utilizing the record to interactively generate a plurality of questions relating to a health condition of the patient;

transmitting, in voice generated form, the plurality of questions relating to the health condition of the patient to the patient;

at the telephone, responding to each of the plurality of questions relating to the health condition of the patient;

transmitting each response to the central monitoring system;

at the central monitoring system, receiving and decoding each response and thereafter storing each response in the record;

processing each response received; and automatically alerting a health care provider if the patient requires an appointment.

14. A computer-based patient initiated method to report health status of a patient to a central monitoring system, the central monitoring system including a computer processor, the method comprising the steps of:

initiating a monitoring session by remotely accessing the central monitoring system with a telephone;

at the central monitoring system, retrieving a record for the patient;

at the central monitoring system, utilizing the record to generate a plurality of questions relating to a health condition of the patient;

transmitting, in voice generated form, the plurality of questions relating to the health condition of the patient to the patient;

at the telephone, responding to each of the plurality of questions relating to the health condition of the patient;

transmitting each response in voice form to the central monitoring system; and at the central monitoring system, receiving and decoding each voice response and thereafter storing each response in the record;

processing each response received; and during the monitoring session, automatically alerting the patient at the telephone if the patient requires an appointment.

15. A patient-initiated system for monitoring the health condition of a patient, comprising:

a telephone operated by a patient speaking in numbers, the numbers representing a health condition of the patient, the patient utilizing the telephone to initiate an interactive health care communication session at a time convenient to the patient by calling a central monitoring system; and a central monitoring system coupled via a communications system to the telephone for interacting with the patient during the interactive health care communication session, and answering the call initiated by the patient at the telephone, in response thereto the central monitoring system generating a plurality of questions concerning the health condition of the patient for the patient to answer by speaking in numbers at the telephone, and storing answers to the plurality of questions for later retrieval, the central monitoring system including a speech recognition decoder receiving and decoding the numbers spoken by the patient at the telephone and transmitted over the communications system to the central monitoring system, a computer processor coupled to the speech recognition decoder, a voice generator coupled to the computer processor generating voice output under the control of the computer process, said voice output transmitted over the communications system to the touch-tone telephone, a database coupled to the computer processor storing a patient record representing the health condition of the patient and storing the plurality of questions concerning the health condition of the patient, wherein the computer processor retrieves the plurality of questions concerning the health condition of the patient from the database and causes the voice generator to generate voice output representing the plurality of questions, wherein the patient responds to the plurality of questions and the computer processor storing information concerning the health condition of the patient in the patient record, which information can be reported to a health care provider to enable the health care provider to then make a diagnosis of the patient's health condition.

16. A patient-initiated drug compliance system to monitor compliance by a patient in taking prescribed drugs, comprising:

a telephone operated by a patient and enabling the patient to initiate at a time convenient to the patient, between the patient and a central monitoring system, a session for monitoring drug compliance,; and a central monitoring system coupled via a telecommunications system to the telephone, the central monitoring system generating a plurality of questions concerning compliance by the patient in taking prescribed drugs for the patient to answer by speaking responses at the telephone, and storing answers to the plurality of questions for later retrieval, the central monitoring system including a decoder receiving and decoding the spoken responses of the patient transmitted over the telecommunications system to the central monitoring system, the spoken responses representing compliance by the patient in taking a prescribed drug, a computer processor coupled to the decoder, a voice generator coupled to the computer processor generating voice output under the control of the computer process, said voice output transmitted over the telecommunications system to the telephone, a database coupled to the computer processor storing a patient record reflecting compliance by the patient in taking the prescribed drug and storing the plurality of questions concerning compliance by the patient in taking the prescribed drug, wherein the computer processor retrieves the plurality of questions concerning compliance by the patient in taking the prescribed drug from the database and causes the voice generator to generate voice output representing the plurality of questions, and wherein the patient responds to the plurality of questions using telephone, the computer processor storing information concerning compliance by the patient in taking the prescribed drug in the database.

17. A computer-based system including an automated central monitoring system to report health status of a patient to a health care provider, the system comprising:

means for remotely accessing the central monitoring system;

means for transmitting patient identification information to the central monitoring system;

means, located at the central monitoring system, for receiving the patient identification information, and for comparing the patient identification information with previously stored identification information so to securely identify the patient;

means for retrieving a record for the identified patient;

means, located at the central monitoring system, for utilizing the record and previously received patient responses to dynamically generate a plurality of questions relating to a health condition of the patient;

means, located at the central monitoring system, for transmitting, in voice generated form, the plurality of questions relating to the health condition of the patient to the patient;

means for receiving a response to each of the plurality of questions in either voice form or as a DTMF signal;

means for transmitting each response to the central monitoring system;

means, located at the central monitoring system for determining whether a response is a DTMF signal or a voice response;

means, located at the central monitoring system, for receiving and decoding each response and thereafter storing each response in the record; and means for automatically reporting the health status of a patient to a health care provider.

18. The system of claim 17 further comprising means for recording a patient response if the patient response is received as a voice response which cannot be decoded by the central monitoring system.

19. The system of claim 17 further comprising means for analyzing each patient record.

20. A computer-based patient-initiated method to allow the reporting of health status of a patient to a computerized and automated central monitoring system, the central monitoring system including a computer processor, the method comprising the steps of:

at the central monitoring system, waiting passively for the patient to initiate communication with the central monitoring system;

at a time convenient to the patient, initiating a health status communication session by remotely accessing the central monitoring system with a telephone;

entering, at the telephone, a patient identification information;

transmitting the patient identification information to the central monitoring system;

at the central monitoring system, receiving and decoding the patient identification information;

at the central monitoring system, retrieving a record corresponding to the patient identification number;

at the central monitoring system, utilizing the record to generate a plurality of questions relating to a health condition of the patient;

transmitting, in voice generated form, the plurality of questions relating to the health condition of the patient to the telephone;

at the telephone, responding to each of the plurality of questions relating to the health condition of the patient;

transmitting each response as either DTMF signals or spoken voice signals to the central monitoring system;

at the central monitoring system, ascertaining whether a response is a DTMF signal or spoken voice signal;

at the central monitoring system, receiving and decoding each response and thereafter storing each response in the record, which stored responses can automatically be reported to a health care provider to enable the health care provider to then make a diagnosis of the patient's condition.

21. The method of claim 20 further comprising the step of recording a patient response if the patient response is received as a voice signal which cannot be decoded by the central monitoring system.

* * * * *